US009974598B2

(12) United States Patent
Janssen et al.

(10) Patent No.: US 9,974,598 B2
(45) Date of Patent: May 22, 2018

(54) COATING SYSTEM COMPRISING $ZRO_2$ FOR ELECTROSURGICAL DEVICES

(71) Applicant: Oerlikon Surface Solutions AG, Trübbach, Trübbach (CH)

(72) Inventors: Albert Peter Gerhard Janssen, Chur (CH); Volker Derflinger, Feldkirch (AT); Canet Acikgoz, Bad Ragaz (CH)

(73) Assignee: Oerlikon Surface Solutions AG, Pfäffikon, Pfäffikon (CH)

( * ) Notice: Subject to any disclaimer, the term of this patent is extended or adjusted under 35 U.S.C. 154(b) by 201 days.

(21) Appl. No.: 14/785,305

(22) PCT Filed: Apr. 15, 2014

(86) PCT No.: PCT/EP2014/001003
§ 371 (c)(1),
(2) Date: Oct. 16, 2015

(87) PCT Pub. No.: WO2014/170011
PCT Pub. Date: Oct. 23, 2014

(65) Prior Publication Data

US 2016/0074094 A1 Mar. 17, 2016

(30) Foreign Application Priority Data

Apr. 17, 2013 (DE) ........................ 10 2013 006 598

(51) Int. Cl.

| | |
|---|---|
| ***C23C 14/35*** | (2006.01) |
| ***A61B 18/14*** | (2006.01) |
| ***C23C 14/00*** | (2006.01) |
| ***C23C 14/08*** | (2006.01) |
| ***C23C 14/32*** | (2006.01) |
| ***C23C 14/34*** | (2006.01) |
| *A61B 18/00* | (2006.01) |
| *A61B 18/12* | (2006.01) |

(52) U.S. Cl.
CPC .......... *A61B 18/14* (2013.01); *C23C 14/0036* (2013.01); *C23C 14/083* (2013.01); *C23C 14/325* (2013.01); *C23C 14/345* (2013.01); *C23C 14/35* (2013.01); *A61B 2018/0041* (2013.01); *A61B 2018/00083* (2013.01); *A61B 2018/00101* (2013.01); *A61B 2018/00107* (2013.01); *A61B 2018/00119* (2013.01); *A61B 2018/00577* (2013.01); *A61B 2018/00589* (2013.01); *A61B 2018/00601* (2013.01); *A61B 2018/126* (2013.01); *A61B 2018/1253* (2013.01); *A61B 2018/144* (2013.01); *A61B 2018/1412* (2013.01)

(58) Field of Classification Search
CPC .......... A61B 18/14; A61B 2018/00083; A61B 2018/00101; A61B 2018/00107; A61B 2018/00119; A61B 2018/0014; A61B 2018/00577; A61B 2018/00589; A61B 2018/00601; A61B 2018/1253; A61B 2018/126; A61B 2018/1412; A61B 2018/144; C23C 14/0036; C23C 14/083; C23C 14/345; C23C 14/35
USPC ........................................................ 606/41–50
See application file for complete search history.

(56) References Cited

U.S. PATENT DOCUMENTS

| | | | | |
|---|---|---|---|---|
| 5,356,408 | A | 10/1994 | Rydell | |
| 2001/0012936 | A1 * | 8/2001 | Heim .................... | A61B 18/14 606/45 |
| 2002/0013591 | A1 * | 1/2002 | Fleischman ............ | A61B 17/11 606/155 |
| 2003/0130653 | A1 | 7/2003 | Sixto, Jr. et al. | |
| 2010/0183900 | A1 | 7/2010 | Wallin et al. | |

FOREIGN PATENT DOCUMENTS

| | | | |
|---|---|---|---|
| DE | 4212053 | C1 | 1/1996 |
| DE | 202012008484 | U1 | 11/2012 |
| EP | 0517244 | A1 | 12/1992 |
| EP | 1905370 | A1 | 4/2008 |
| WO | 9320747 | A1 | 10/1993 |
| WO | 9408524 | A1 | 4/1994 |

* cited by examiner

*Primary Examiner* — Michael Peffley
*Assistant Examiner* — Khadijeh Vahdat

(57) ABSTRACT

A coating system comprising at least one layer made at least essentially of $ZrO_2$ which is used for providing insulating properties to parts of medical devices, particularly of electrosurgical devices.

15 Claims, No Drawings

COATING SYSTEM COMPRISING $ZRO_2$ FOR ELECTROSURGICAL DEVICES

FIELD OF THE INVENTION

The present invention relates to a coating system containing $ZrO_2$ and method for applying this coating system to surfaces of parts of electrosurgical devices which need to be electrically insulating.

BACKGROUND OF THE INVENTION

Electrosurgery is the process of using the direct application of electric currents to cut and/or desiccate tissue and stop blood flow. It has been in use for a number of years, but it is constantly being perfected and revolutionized.

Electrosurgery is utilized for all different types of procedures in the medical industry today. Some of these include dermatological, cardiac, vascular, orthopedic, and dental surgeries. It is especially useful in situations and in areas of the body where cutting can induce a great deal of blood loss.

Because it has the power to coagulate the vessels around an incision, it can minimize blood loss. Since the introduction of electrosurgery in the 1920's many surgeries have been enabled because electrosurgical tools can control bleeding while the use of a scalpel cannot control bleeding.

In principle, it can be differentiated between the monopolar electrosurgery and the bipolar electrosurgery.

In the monopolar electrosurgery a single electrode or pencil/instrument is used for carrying the electrical current to the surgical or incision site. This current travels through the body of the patient to the patient who is grounded. Higher voltages are used for coagulation while lower voltages are used for cutting. However in the bipolar electrosurgery the patient's body is not used as a conductor to carry current and for this reason this technique is most appropriate where the spread of thermal damage to adjacent tissues creates the potential for patient harm. Excessive thermal spread could, for example, damage an adjacent nerve to the body's region being operated.

By applying bipolar electrosurgery techniques, usually, current is delivered through one tip of a bipolar instrument and is returned back to the generator through the opposing, tip of the instrument.

Nowadays, many modern medical devices use integrated electrical circuitry, and it is important that they are properly insulated. The risk of injury from electrical shock to the surgeon and the patient can be extremely high if the metal components are not properly insulated.

The patent document WO 93/20747 discloses a guide wire for supporting monopolar arcing for cutting tissue and for ablating occlusions which includes a flexible metal wire (which is a corrosion-resistant metal or alloy, such as stainless steel) including a distal end, an electrically insulating coating which is extended along the wire, and an electrically and thermally insulating tip having a distal end and which is attached to the wire, and the wire is extended through the electrically and thermally insulating tip and forms an electrode at the distal ends of the wire and the tip. The insulating coating must be according to WO 93/20747 a medically compatible electrical insulator, such as polyurethane, polyimide, polyethylene, and preferably tetrafluoroethylene (TEFLON) because of its very good sliding properties. Furthermore, the insulating coating must be sufficiently thick to protect a surgeon using the guide wire and the patient from electrical shock and at the same time sufficiently thin so that the insulated wire fits into small lumens.

The patent document EP1905370 discloses an electrosurgical instrument and, more particularly, coatings for an electrosurgical instrument which uses thermogenic energy for cauterization, coagulation and tissue joining/welding in combination with staples to form a hemostatic staple/coagulation/cut line tissue. In accordance with EP1905370 the electrosurgical instrument has an end effector which can have a first pole electrode and a second pole electrode and a staple cartridge having at least one staple therein, depending on the type of energy received by the end effector. However, in all cases the electrosurgical instrument comprises a non-conducting or dielectric coating which can be placed depending on the type of construction of the instrument:

- on at least a part of the second pole electrode, or
- on at least one of the first and second pole electrodes where the dielectric coating can prevent direct tissue contact with at least one of the electrically active electrodes, or
- on at least one staple of the staple cartridge for reducing formation of a surface charge thereon during application of bipolar energy to tissue.

The non-conducting or dielectric coating according to EP1905370 could be but is not limited to a polytetrafluoroethylene (PTFE), titanium dioxide, or polymers based on paraxylene, or an epoxy.

Furthermore, it is known from the state of the art, that today some electrosurgical instruments, such as bipolar electrical surgical scissors, are being coated with $Al_2O_3$ coatings deposited by thermal spray techniques. However, this practice can be complex and is very expensive.

The objective of the present invention is to provide a coating system and method for producing insulating coatings which preferably exhibit simultaneously good wear resistance and/or good sliding properties. Furthermore, it is an objective of the present invention to provide an advantageous method for producing the coating systems according to the present invention which allows coating parts of electrosurgical devices which can have different forms and dimensions in an uncomplicated and not expensive way.

SUMMARY OF THE INVENTION

The objective of the present invention was achieved by providing a coating system containing at least one layer of zirconium dioxide, $ZrO_2$, deposited by means of arc evaporation PVD techniques or magnetron sputtering PVD techniques. In the case of using magnetron sputtering PVD techniques, then preferably high power impulse magnetron sputtering (HIPIMS) techniques.

DETAILED DESCRIPTION OF THE PREFERRED EMBODIMENTS $ZrO_2$-containing coating systems according to the present invention can be applied on the surface of parts of medical devices that require electrical insulation, e.g. electrosurgical devices, such as mono- and bipolar surgical instruments.

$ZrO_2$-containing coating systems according to the present invention are particularly ideal for providing dielectric insulating properties to medical devices and instruments such as blades, cutters and ablators, as well as bipolar and monopolar devices and also medical electronics in general.

$ZrO_2$-containing coating systems according to the present invention have more reliable properties than heat-shrink tubing and polymer over moulding and are therefore most suitable for coating electrosurgical instruments.

A $ZrO_2$ layer forming a coating system according to the present invention, or included in a coating system according to the present invention exhibits preferably a dielectric constant of about 18.4 and/or a high voltage breakdown of about 0.60 kV and/or a breakdown current of about 20 mA.

A preferred embodiment of a $ZrO_2$-containing coating system according to the present invention comprises at least one zirconium nitride layer. Preferably the ZrN-layer is deposited as interlayer and/or support layer between the substrate surface and the $ZrO_2$-layer.

A preferred method for depositing a $ZrO_2$ layer according to the present invention involves the use of arc evaporation techniques for evaporating targets (at least one target) made of zirconium or comprising mainly zirconium in a reactive oxygen-containing atmosphere for forming $ZrO_2$ on the substrate surface. Furthermore, preferably at least during the deposition of the $ZrO_2$-layer a pulsed bias voltage is applied to the substrate.

A $ZrO_2$-layer deposited by reactive arc ion plating PVD techniques according to the above mentioned embodiment of a method according to the present invention exhibits droplets containing at least mostly or mainly zirconium. The droplets are melted material from the target which could not be evaporated properly and consequently could not react properly with the reactive gas (in this case oxygen) for forming the desired coating material (in this case $ZrO_2$). The $ZrO_2$-layer deposited in this way exhibited a particularly good performance.

In a preferred embodiment of a coating system comprising at least one arc-PVD-deposited $ZrO_2$-layer according to the present invention the total thickness of the $ZrO_2$-layer is not greater than 30 nm, preferably not greater than 20 μm, more preferably not greater than 10 μm.

The thickness of an arc-PVD-deposited $ZrO_2$-layer for a coating system according to the present invention must be so selected, that the $ZrO_2$-layer can provide sufficient isolation. For this purpose it is necessary to take into account the surface quality of the surface to be coated and also the porosity of the $ZrO_2$ coating.

Particularly, very good results were attained in the context of the present invention by producing coating systems which contain at least one arc-PVD-deposited $ZrO_2$-layer having a thickness of at least 3 μm, more particularly of at least 4 μm or 5 μm.

A further preferred method for depositing a $ZrO_2$ layer for a coating system according to the present invention involves at least one step in which at least one Zr-target is sputtered by using HIPIMS-techniques in an oxygen-containing atmosphere and by applying a pulsed bias voltage to the substrate which is being coated during the $ZrO_2$-deposition.

Coating systems comprising at least one layer made at least essentially of $ZrO_2$ according to the present invention may be used for providing electrically insulating properties to parts of medical devices, or at least pans of medical components or instruments, which may be electrosurgical devices or which may be comprised in electrosurgical devices.

Particularly, a coating system according to the present invention could be used for avoiding electrical shock of the persons which are in contact with the medical device during its use.

The present invention also includes methods for coating substrates.

The invention claimed is:

1. A coating system having electrically insulating properties deposited on a surface of an electrically conductive substrate which is a part of a medical device, particularly of an electrosurgical device, the coating system comprising:
at least one zirconium dioxide layer comprising droplets which consist essentially of zirconium, wherein the droplets are melted material from a target which was not evaporated properly and which consequently did not react properly with reactive oxygen gas for forming $ZrO_2$, and
wherein the at least one zirconium dioxide layer renders the surface of the electrically conductive substrate electrically non-conductive.

2. The coating system according to claim 1, wherein the at least one zirconium dioxide layer exhibits a dielectric constant of about 18.4 and/or high voltage breakdown of about 0.60 kV and/or a breakdown current of about 20 mA.

3. The coating system according to claim 1, wherein a thickness of the at least one zirconium dioxide layer is less than 30 μm.

4. The coating system according to claim 3 wherein the thickness of the at least one zirconium dioxide layer is at least 3 μm.

5. The coating system according to claim 1, wherein the coating system further comprises at least one zirconium nitride layer.

6. The coating system according to claim 5, wherein the zirconium nitride layer is deposited between the surface of the electrically conductive substrate and the at least one zirconium dioxide layer as an interlayer and/or as a support layer.

7. The coating system according to claim 1, wherein the surface of the electrically conductive substrate is at least a part of a surface of an electrode.

8. The coating system according to claim 1, wherein the electrically conductive substrate is a wire of a guide wire.

9. The coating system according to claim 1, wherein the coating system is deposited on the surface of a medical device selected from the group consisting of a blade, a cutter, an ablator a monopolar electrosurgical instrument, and a bipolar electrosurgical instrument.

10. The coating system according to claim 9, wherein the medical device includes, an electrode formed of a metal wire and at least a tip attached to the wire whereat the electrode offers a contact surface to be in contact with tissue of a patient, and the coating system is deposited on at least a part of a surface of the electrode in such a way that electrical conductivity of the coated electrode surface is reduced and consequently thermal energy at the electrode contact surface is also reduced in order to avoid damages of the tissue.

11. The coating system according to claim 9, wherein the medical device includes a surface of an electrode which can be in contact with a patient body or with a body of an operator of the medical device and the coating system is deposited on at least a part of this surface in order to avoid an electrical shock of the patient or of the operator.

12. The coating system according to claim 9, wherein the coating system is applied to one or more surfaces of the medical device in order to avoid a short of the medical device during operation.

13. The coating system according to claim 9, wherein the medical device is used for cutting tissue and/or for ablating occlusions.

14. A method for forming a coating system, comprising:
depositing at least one zirconium dioxide layer comprising droplets consisting essentially of zirconium on a surface of an electrically conductive substrate which is part of a medical device, particularly of an electrosurgical device, using physical vapour deposition techniques including arc evaporation of targets consisting essentially of zirconium in an oxygen-containing atmosphere, and applying a pulsed bias voltage to the surface of the electrically conductive substrate during deposition of the at least one zirconium dioxide layer, wherein the at least one zirconium dioxide layer renders the surface of the electrically conductive substrate electrically non-conductive, and wherein the droplets are melted material from the targets which was not evaporated properly and which consequently did not react properly with reactive oxygen gas for forming $ZrO_2$.

15. The method according to claim 14, comprising using high power impulse magnetron sputtering techniques to deposit at least one layer on the surface of the electrically conductive substrate.

* * * * *